| United States Patent [19] | [11] Patent Number: 4,892,959 |
|---|---|
| Champion et al. | [45] Date of Patent: Jan. 9, 1990 |

[54] METHOD FOR THE PRODUCTION OF N-METHYLPYRROLIDINE

[75] Inventors: Donald H. Champion, Pflugerville; John F. Knifton; Wei-Yang Su, both of Austin, all of Tex.

[73] Assignee: Texaco Chemical Co., White Plains, N.Y.

[21] Appl. No.: 184,660

[22] Filed: Apr. 22, 1988

[51] Int. Cl.$^4$ .......................................... C07D 295/02
[52] U.S. Cl. .................................................. 548/579
[58] Field of Search ........................................ 548/529

[56] References Cited

U.S. PATENT DOCUMENTS

| 3,190,922 | 6/1965 | Le Bard et al. | 564/488 |
| 3,444,204 | 5/1969 | Schutt | 564/447 X |
| 4,448,998 | 5/1984 | King | 564/420 X |

FOREIGN PATENT DOCUMENTS

| 2813162 | 9/1979 | Fed. Rep. of Germany | 548/579 |
| 0088464 | 5/1984 | Japan | 548/579 |
| 0193515 | 3/1967 | U.S.S.R. | 548/579 |

OTHER PUBLICATIONS

Wojcik et al., J.A.C.S., 56, (1934), pp. 2419–2424.

*Primary Examiner*—Joseph Paul Brust
*Attorney, Agent, or Firm*—Jack H. Park; Kenneth R. Priem; Cynthia L. Kendrick

[57] ABSTRACT

A method is disclosed for the improved production of N-methylpyrrolidine at moderate conditions which comprises the steps of reacting N-methylpyrrolidone with hydrogen over a copper chromite catalyst at a moderate temperature and a pressure of 1000 psig to 5000 psig and thereafter isolating the N-methylpyrrolidine by extraction with an aliphatic hydrocarbon solvent having a boiling point less than 70° C. or greater than 90° C.

7 Claims, No Drawings

METHOD FOR THE PRODUCTION OF N-METHYLPYRROLIDINE

FIELD OF THE INVENTION

This invention relates to a process for the preparation of pyrrolidines by hydrogenation of pyrrolidones over a copper chromite catalyst.

More specifically, this invention concerns the hydrogenation of N-methylpyrrolidone to N-methylpyrrolidine over a copper chromite catalyst at moderate conditions. High pyrrolidine selectivities were observed and selective extraction of the product mixture was accomplished using hydrocarbons having a boiling point in a specified range.

BACKGROUND OF THE INVENTION

Hydrogenation of amides over copper chromite is known in the art. In an article by Wojcik, B. and Adkins, H. in *J. Am. Chem. Soc.* 1934, 56, 2419-24 there is a general discussion of hydrogenation of amides over copper chromite. The authors of this work came to the conclusion that a diluent such as dioxane was necessary for the by-product water in order to make this process function satisfactorily.

In Pat. No. 3,190,922 (1965) to LeBard, N. M. et al., there is disclosed a process for hydrogenation of N,N-dialkyl amides at low pressures over copper chromite. In this process the water which is produced is continually removed. As pointed out Col. 1, lines 30-36, typically this reaction is carried out at a pressure greater than 200 atmospheres with dioxane as the solvent. This work does not appear to contemplate hydrogenation of lactams.

Deterrents to those in the art desiring to commercialize such a process include the high pressure, handling and removing the solvent, inability to recycle and the number of side reactions which limit the yield and purity.

U.S. Pat. No. 3,444,204 to Schutt et al. discloses a process for the continuous production of higher alkyl-tertiary amines over a copper chromite catalyst in the presence of solvents using at least a 50-fold excess of hydrogen. In this reference the flow rate of amides was 0.07 to 0.33/ml/ml cat./h. The use of lactams was not taught or suggested in this reference.

King discloses in U.S. Pat. No. 4,448,998 a process for producing tertiary amines containing from about 10 to about 72 carbon atoms by hydrogenation of the corresponding N,N-disubstituted amides over a copper chromite-zeolite catalyst. Improvements in conversion and selectivity are attributed to the zeolite. Again, the use of lactams was not contemplated.

In German Pat. No. 28 13 162, Schroeder, W. and Mercker, H. J. teach the continuous hydrogenation of N-methylpyrrolidone over copper on alumina at a flow rate of 0.11-0.33 ml/ml cat./h. The German reference suggests that the use of pressure over 3500 psig is necessary for this type of reaction. The pressure used, as reported in the examples, is about 3626 psi. It is noted that the conversion is high, but overall productivity is relatively low. Removal of by-product water is apparently accomplished by using caustic.

It would be an advance in the art if a process for the hydrogenation of N-methylpyrrolidone could be accomplished under milder conditions and, in addition, exhibit improved productivity. It would be especially desirable if such a process would lend itself to recycling and continuous conversion.

The instant invention provides a method for producing pyrrolidines from pyrrolidones. In particular high selectivities to N-methylpyrrolidine are observed using lower pressure and moderate temperature. Higher space velocities result in higher yield per catalyst volume compared with the closest art. An additional feature is that the pyrrolidine product can be isolated by extraction of the product mixture by specified hydrocarbons followed by distillation, and the hydrocarbon used as the extraction solvent can be recycled. As mentioned, the art suggests removal of water from the product by using a caustic.

SUMMARY OF THE INVENTION

In accordance with the present invention pyrrolidones were hydrogenated to pyrrolidines over a copper chromite catalyst at a temperature of about 150°-350° C. and a pressure range of about 1000-5000 psig. Selectivities to the corresponding pyrrolidines varied, depending upon the substituent attached to the nitrogen atom in the pyrrolidone used as the reactant.

The productivity is on the order of 3 to 5 times as high as the closest available art using a pressure of about 1000 psig lower than the closest art.

In addition an improved method of extraction of the product is demonstrated using specified hydrocarbons.

DETAILED DESCRIPTION OF THE PREFERRED EMBODIMENT

In the narrower and more preferred practice of this invention pyrrolidines are prepared from pyrrolidones by a process which comprises reacting an N-substituted pyrrolidone over a copper chromite catalyst at a temperature of about 150° C. to 350° C. and a pressure of about 1000 psig to 5000 psig and recovering the product by extracting the product with an inert solvent which can readily be separated from the N-substituted pyrrolidine by distillation and which is selective for the extraction of N-substituted-pyrrolidine from water.

The process can be carried out continuously and unreacted pyrrolidone recovered and recycled.

The general reaction can be represented by:

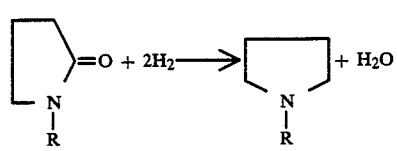

(Eq. 1)

Recovery of the N-substituted pyrrolidine can be carried out by removal of water by extraction with an inert solvent or by drying over sodium hydroxide. Said solvent may be a hydrocarbon solvent, either an aromatic or aliphatic hydrocarbon moiety. Suitable solvents may include pentane, hexane, isooctane, isopentane, n-dodecane, n-decane, cyclohexane, cyclododecane, n-hexadecane, 2,2,4-trimethylpentane, as well as mixtures thereof, aromatic solvents such as benzene, toluene, xylenes, ethylbenzene, cumene, triisopropylbenzene, diethylbenzene, durene, dimethylstyrenes and alkyltoluenes, together with solvent mixtures such as Texaco's TEXSOLVE® B, TEXSOLVE® L OR TEXSOLVE® V.

For the recovery of N-methylpyrrolidine from unreacted N-methylpyrrolidone etc., it is preferable to use a hydrocarbon solvent of boiling point less than 70° C., or above 90° C., particularly in the range 90°–80° C., in order to have a solvent sufficiently different in boiling point from the reactant (N-methylpyrrolidone) and product as to facilitate separation by distillation. Preferably said solvent should be immiscible with the crude product mixture.

The most preferred solvent for N-methylpyrrolidine synthesis and recovery is pentane. The usefulness of this solvent is illustrated in the accompanying examples, particularly Examples 5 and 6.

In general, the components of this invention include an N-substituted pyrrolidone reactant, hydrogen, a copper chromite catalyst, and an extractive solvent.

Selectivities to desired N-substituted pyrrolidine products vary depending on the substituent attached to the nitrogen atom of the pyrrolidone. This is demonstrated in Example 2, Table I.

N-substituted pyrrolidones which can be used include those of the formula:

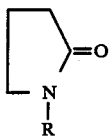

where R represents hydrogen, an alkyl or hydroxyalkyl group having 1 to 8 carbon atoms, or a cycloalkyl group having from 5 to 8 carbon atoms. Specific examples which provided desirable results included N-cyclohexylpyrrolidone, N-ethylpyrrolidone, N-2-hydroxyethylpyrrolidone, pyrrolidone itself and N-methylpyrrolidone. Good results were obtained with N-methylpyrrolidone.

The copper chromite catalyst used in the present invention is known in the hydrogenation art. The preparation of catalysts of this type is discussed in an article by Connors, Folkers and Adkins in the Journal Of The American Chemical Society, Vol. 54., pp. 1113–45 (1932), and in "Reactions of Hydrogen with Organic Compounds Over Copper-Chromium Oxide and Nickel Catalysts" by Homer Adkins, University of Wisconsin Press, Madison, Wis. (1937). There is also a discussion of the nature of the catalyst in an article by Adkins, Burgoyne and Schneider in the Journal of the American Chemical Society, Vol 72, pp. 2626–29 (1950). Preferred catalysts contain 40 to 65% CuO and 35 to 60% $Cr_2O_3$, and optionally, a promoter such as barium, magnesium, manganese or calcium oxides. There are copper chromite catalysts which are available commercially which perform satisfactorily in the process. For example, commercial copper chromite catalysts include Calsicat E-105P and Harshaw Cu-1186 ⅛". Calsicat E-105P is a copper chromite powder from Mallinckrodt Inc. Company, containing 47% each of copper and chromium oxides and having a surface area of 30–70 $m^2/g$. Harshaw Cu-1186 T ⅛" is a prereduced copper chromite tablet from Harshaw containing copper oxide (42%), chromium oxide (44%) and barium oxide (9%) and having a surface area of 90 $m^2/g$ and an apparent bulk density of 1.40 g/cc.

It will be understood that the shape and dimensions of the catalysts are not critical and that powders, tablets or extrudates of any suitable shape may be used.

The powdered or pelleted catalyst compositions of the present invention are preferably employed as a fixed bed of catalyst in a continuous reaction system. In a continuous process of this nature, the time of contact of the reactants with the catalyst is one of the interrelated factors that those skilled in the art will adjust, along with reactor geometry, bed geometry, pellet size, etc. in order to obtain a desired selectivity and rate of reaction giving a desired percentage of conversion of the reactants. Thus, it is not necessary to drive the reaction to completion because unreacted feedstock components can be recycled to the reactor.

It was found in the instant invention that one factor which contributed to improved productivity was holding the conversion down to some extent. This was accomplished by adjusting the space velocity. Compared with the closest art, the space velocity was from about 1.2 to 33 times as great. The productivity was found to be about twice or three times as high by adjusting the space velocity in combination with the other components of the instant invention, including lower pressure.

The amount of catalyst employed in the process is not critical. A greater amount of catalyst may be expected to decrease the reaction time. Catalyst usage in amounts of 5% to 20 wt % of the catalyst based on weight of pyrrolidone is generally sufficient in batch processing.

The reaction temperature should be in the range from 150° C. to 350° C. and preferably from 220°–300° C.

It is desirable to maintain a pressure of from about 1000 to 5000 psig. Preferably the pressure should be maintained in the range of 2000–3000 psig. The fact that good productivity can be achieved using lower pressures is a desirable feature of the instant invention.

Another desirable aspect of the instant invention is an improved method of isolating the product by selective extraction from water. A survey of the art indicates caustic can be used to extract water in this type reaction. However it has been discovered that extraction of the product mixture with certain hydrocarbons followed by distillation allows isolation of dry N-substituted pyrrolidine and the extraction solvent can be reused. This alleviates the problem of caustic disposal and regeneration or disposal of a drying agent. In particular, hydrocarbons having a boiling point in a range which allows for their separation from the reactant and product by distillation can be used for this purpose.

The product can also be isolated by conventional methods such as drying over sodium hydroxide.

The invention will be illustrated by the following examples which demonstrate the improvements in catalytic activity obtained by using the process of the instant invention. High selectivity to N-methylpyrrolidine in particular is observed at moderate conversions.

The data in the following examples indicate that higher space velocities result in higher selectivity as conversion decreases. There is an optimum point at which the yield is greatest by compromising these factors. It is desirable to use conditions which give the greatest conversion at about 100% selectivity, depending on the quality of product desired. Under these conditions higher productivity can be obtained than disclosed in the closest prior art.

It is understood the examples are only intended as a means of illustration and are not intended to limit the invention in any way.

EXAMPLE 1

N-methylpyrrolidone (50.0 g) and copper chromite powder (3.46 g of Calsicat E-105P) were charged to a glass liner and placed in a batch, rocking, autoclave. The autoclave was purged with hydrogen. After admitting hydrogen to 200 psig the autoclave was heated to 285° C. and hydrogen was admitted to a pressure of 2000 psig. The pressure dropped to 1250 psig after 1 hr. A 46% conversion of N-methylpyrrolidone and a 94% selectivity to N-methylpyrrolidine were calculated from CG area percents (water free) of the product.

EXAMPLE 2

N-methylpyrrolidone (100 g) was hydrogenated over copper chromite powder (6.90 g of Calsicat E-105P) at 281°-5° C. and 3000 psig for 6 hr in a 300 cc stirred autoclave. Conversion and selectivity were calculated as in Example 1. Various other pyrrolidones were hydrogenated in the same manner giving the results in Table I. The selectivities varied depending on the substituent attached to the nitrogen atom. Equation 1 depicts the general reaction.

TABLE I

| Substituent R | Reaction Temperature | Reaction Time | Conversion | Selectivity |
|---|---|---|---|---|
| methyl | 280-5° C. | 6.0 hr | 85% | 85% |
| cyclohexyl | 283-6 | 6.5 | 90 | 56 |
| ethyl | 276-85 | 8.5 | 85 | <77 |
| 2-hydroxyethyl | 282-90 | 6.0 | 43 | 40 |
| hydrogen | 281-5 | 6.0 | 95 | 33 |

EXAMPLE 3

Copper chromite tablets (140 cc of Harshaw Cu-1186 ⅜") were charged to a 1" ID stainless steel continuous reactor and activated by passing ca. 3% hydrogen in nitrogen through the bed with gradual heating until an exotherm was observed moving through the catalyst bed. The hydrogen concentration was then gradually increased to 100% as the reactor temperature was maintained at 150° C. N-methylpyrrolidone and hydrogen were passed through the reactor in an upflow configuration. Conditions were maintained for a minimum of 2 hr. before each GC sample of the effluent was obtained. Conversions and selectivities were calculated from water free GC area percents and are given in Table II.

It may be noted that in this Example, N-methylpyrrolidine is obtained in 100% selectivity and high space velocities (in the range of LHSV's of 0.4-3.6). Consequently the yield per catalyst volume is in the region of three times that of the closest prior art.

TABLE II

| Reactor Temperature | N—Methylpyrrolidone Feed Rate | Hydrogen Feed Rate | Pyrrolidone Conversion | N-methylpyrrolidine Selectivity |
|---|---|---|---|---|
| 180°C. | 0.48 lb/h | 120 l/h | 6% | 100% |
| 240 | 0.40 | 120 | 76 | 96 |
| 260 | 0.44 | 120 | 78 | 93 |
| 280 | 0.44 | 120 | 80 | 89 |
| 300 | 0.42 | 120 | 82 | 85 |
| 240 | 0.12 | 120 | 97 | 98 |
| 240 | 0.30 | 120 | 61 | 98 |
| 240 | 0.44 | 120 | 50 | 100 |
| 240 | 1.16 | 120 | 23 | 100 |
| 240 | 0.20 | 209 | 93 | 99 |
| 240 | 0.44 | 209 | 48 | 99 |

EXAMPLE 4

N-methylpyrrolidine was hydrogenated as in Example 3 at 240° C. with N-methylpyrrolidone and hydrogen feed rates of 0.33 lb/h and 209 l/h, respectively. The product (3382 g), consisting of 17.2% water, 40% N-methylpyrrolidine and 43% N-methylpyrrolidone by weight, was distilled through a 19" column packed with mesh saddles giving distillate (142 lg) boiling at 72°-5° C. which contained 9.8 wt % water and gave an amine assay of 10.5 meq/g.

More careful distillations of product mixture through a 19" or 40" column gave distillates boiling at 72°-4° C. The distillates contained 8.1-8.2 wt % water. They were combined, dried over sodium hydroxide and distilled giving 98.4 GC A % (water free basis) pure N-methylpyrrolidine containing 0.28 wt % water.

EXAMPLE 5

Samples of a mixture of N-methylpyrrolidine (42.4), N-methylpyrrolidone (49.0) and water (8.6 wt %) similar to the products of Example 3, Table II, having ca. 50% N-methylpyrrolidone conversion, were shaken with approximately equal volumes of several hydrocarbons. Formation of two layers occurred in several cases. GLC analysis of the layers are given in Table III.

TABLE III

| | Water | N—Methylpyrrolidine | N—Methylpyrrolidone | Solvent |
|---|---|---|---|---|
| Pentane | | | | |
| upper layer | 0.0 | 32.4 | 4.5 | 62.8 |
| lower layer | 12.9 | 10.8 | 73.5 | 2.5 |
| Isooctane | | | | |
| upper layer | 0.0 | 32.8 | 4.7 | 62.4 |
| lower layer | 12.1 | 10.9 | 75.4 | 1.1 |
| Diethylbenzene | | | | |
| upper layer | 1.1 | 25.2 | 20.9 | 52.1 |
| lower layer | 16.6 | 13.4 | 61.1 | 8.7 |
| Triisopropylbenzene | | | | |
| upper layer | 0.0 | 26.4 | 9.1 | 64.5 |
| lower layer | 15.1 | 11.5 | 71.1 | 2.2 |

Toluene, xylene, ethylbenzene and cumene did not provide two layers by this method. Addition of a small amount of water, however, caused a phase separation of the toluene and xylene solutions. GLC analysis of the top layers indicated 2.7% water, 25.1% N-methylpyrrolidine, 11.5% N-methylpyrrolidone and 60.7% toluene in the former and 0.5% water, 23.5% N-methylpyrrolidine, 6.2% N-methylpyrrolidone and 69.1% xylene in the latter. Two layers were also formed on addition of water to the ethylbenzene and cumene solutions.

It is evident from these data that a satisfactory recovery of N-methypyrrolidine can be achieved with pentane, isooctane, diethylbenzene and triisopropylbenzene, while toluene and xylene may also be useful under certain circumstances.

EXAMPLE 6

The product (2826 g) prepared in Example 4 was extracted with three 1.0 liter portions of pentane. The top layers were combined and distilled providing 99.0 GC A % (water free basis) pure N-methylpyrrolidine (604 g) boiling at 78.C which contained 0.03 wt % water and gave an amine assay of 11.7 meq/g. The lower boiling material consisted of 14 GC A % N-methylpyrrolidine in pentane.

The lower boiling material was used to extract another 2827 g of the product prepared in Example 4. N-methylpyrrolidine (973 g) was collected at 77°–8° C. The distillate contained 0.14 wt % water and gave an amine assay of 11.5 meq/g. It was 97.5 GC A % pure (water free basis).

The bottom layers (3429 g) obtained from the two extraction procedures were combined and distilled until the head temperature exceeded 100° C. GC analysis indicated the bottoms (2300 g) contained 98.2% N-methylpyrrolidone. Water was present in 0.15 wt %.

What is claimed is:

1. A method for the production of N-methylpyrrolidine which comprises the steps of reacting N-methylpyrrolidone with hydrogen, and wherein water is a by-product, over a catalyst consisting of copper chromite wherein the copper chromite catalyst comprises 40 to 65% copper oxide and 35 to 60% chromium oxide having a promoter from the group consisting oxides of barium, magnesium and manganese, at a temperature range of 150°–350° C. and a pressure of 1000 psig to 5000 psig, and thereafter isolating the N-methylpyrrolidine from its aqueous azeotrope by extracting said N-methylpyrrolidine with a hydrocarbon selected from the group consisting of pentane, isooctane, xylene, toluene, diethyl benzene and triisopropyl benzene.

2. The method of claim 1 wherein the copper chromite catalyst is in the form from the group consisting of powders, tablets and extrudates.

3. The method of claim 1 wherein the temperature is between 200° C. and 300° C.

4. The method of claim 1 wherein the pressure is from about 2000 psig to 3000 psig.

5. The method of claim 1 wherein the hydrocarbon solvent is pentane.

6. The method of claim 1 wherein the N-methylpyrrolidine is extracted from the product mixture, leaving by-product water, and isolating the N-methylpyrrolidine from the hydrocarbon solvent by distillation.

7. In a process for production of N-methylpyrrolidine by reacting N-methylpyrrolidine and hydrogen, and wherein water is a by-product, over a catalyst consisting of copper chromite wherein the copper chromite catalyst comprises 40 to 65% chromium oxide and having a promoter from the group consisting of oxides of barium, magnesium and manganese, the improvement comprising the method of isolating the N-methylpyrrolidine by treating the product of the reaction with a hydrocarbon from the group consisting of n-pentane, isooctane, toluene, xylene, diethyl benzene and triisoprophyl benzene to extract the product and isolating the dry N-methylpyrrolidine product by distillation.

* * * * *